United States Patent [19]

Eidenschink

[11] Patent Number: 5,326,495
[45] Date of Patent: Jul. 5, 1994

[54] TETRASUBSTITUTED METHANES HAVING LIQUID-CRYSTALLINE PROPERTIES

[75] Inventor: Rudolf Eidenschink, Gaustrasse, Fed. Rep. of Germany

[73] Assignee: Consortium für elektrochemische Industrie GmbH, Munich, Fed. Rep. of Germany

[21] Appl. No.: 934,539

[22] PCT Filed: Apr. 10, 1991

[86] PCT No.: PCT/EP91/00681
§ 371 Date: Oct. 8, 1992
§ 102(e) Date: Oct. 8, 1992

[87] PCT Pub. No.: WO91/16295
PCT Pub. Date: Oct. 31, 1991

[30] Foreign Application Priority Data

Apr. 12, 1990 [DE]  Fed. Rep. of Germany ....... 4011812

[51] Int. Cl.$^5$ .................. C09K 19/52; C09K 19/34; C09K 19/30; C09K 19/12
[52] U.S. Cl. ................ 252/299.01; 252/299.61; 252/299.63; 252/299.66; 252/299.67; 560/8; 560/55
[58] Field of Search .......... 252/299.01, 299.61, 252/299.63, 299.64, 299.65, 299.66, 299.67; 359/103; 560/8, 55

[56] References Cited

U.S. PATENT DOCUMENTS 4,774,028  9/1988  Imai et al. .............. 252/299.01

OTHER PUBLICATIONS

K. J. Toyne, University of Hull, Liquid Crystal Behavior in Relation to Molecular Structure, pp. 29-62.

C. Destrade, Disc-like Mesogen Polymorphism, pp. 122-146, Mol. Cryst. Liq. Cryst., 1984, vol. 106.

H. Kelker, Chemie Ingenieur Technik, Verfahrenstechnik Techn Chemie, Apparatewesen, 2 Aug.-Heft 1973, Heft 16, pp. 1005-1048.

Technische Anwendungen flüssiger Kristalle.

D. Coates, Standard Telecommunication Laboratories, Materials Requirements for Smetic Liquid Crystal Displays, pp. 99-118.

"Handbook of Liquid Crystals" Schumann, pp. 69-113 edited by Kelker/Rolf Hatz, Basil, 1980.

"Synthesis of Calamitic Liquid Crystals by Transition Metal Catalyzed Cross-Coupling Reaction", Portsch Kontakte (Darmstadt) 1988 (2) pp. 15-28.

"Liquid Crystals" Tschierske et al. vol. 5, No. 1, pp. 177-190 1989.

*Primary Examiner*—Shean Wu

[57] ABSTRACT

Novel tetrasubstituted methane derivatives of the general formula C[—Sp—M—R]$_4$ in which the radicals —Sp—M—R are the same or different, in which Sp is a spacer group selected from an alkylene or alkenylene radical which is unsubstituted or monosubstituted by halogen, —CN or —CF$_3$ or one or two non-adjacent CH$_2$ groups may be replaced by —O—, —CO—, —COO—, —OOC—, —CONH— or —OCOO—, or is a single bond; R is selected from hydrogen, halogen, —CN, —CF$_3$, —OCF$_3$, —NO$_2$, —N(CH$_3$)$_2$, an alkyl or alkenyl radical which is unsubstituted or monosubstituted or polysubstituted by —CN, —NH$_2$, —CF$_3$ or halogen and in which one or more non-adjacent CH$_2$ groups may be replaced by the radicals —O—, —CO—, —OOC—, —COO— or OCOO—; and M is a mesogenic group. Due to their liquid crystal properties, the novel compounds are eminently suitable for use in liquid crystalline media.

18 Claims, No Drawings

TETRASUBSTITUTED METHANES HAVING LIQUID-CRYSTALLINE PROPERTIES

The invention relates to novel tetrasubstituted methanes of the general formula $$C[-Sp-M-R]_4 \quad (I)$$

in which the radicals —Sp—M—R may be identical or different and where

Sp is a spacer element and, in each case independently of the other cases, is an alkylene or alkenylene radical having 1 to 12 carbon atoms which is unsubstituted or monosubstituted by halogen, —CN or —CF$_3$ and in which, in addition, one or two non-adjacent CH$_2$ groups may be replaced by —O—, —CO—, —COO—, —OOC—, —CONH— or —OCOO—, or is a single bond, M is a mesogenic group and R is hydrogen, halogen, —CN, —CF$_3$, —OCF$_3$, —NO$_2$, —N(CH$_3$)$_2$, a straight-chain or branched alkyl or alkenyl radical having 1 to 12 carbon atoms which is unsubstituted or monosubstituted or polysubstituted by —CN, —NH$_2$, —CF$_3$ or halogen and in which one or more non-adjacent CH$_2$ groups may be replaced by the radicals —O—, —CO—, —OOC—, —COO— or —OCOO—.

BACKGROUND OF THE INVENTION

The novel methane derivatives of the general formulae I and II (see below) according to the invention are thermotropic liquid-crystalline compounds; due to their molecular structure principle, which is novel for such compounds, they generally broaden the known range of liquid-crystalline substances by means of which mixtures having favorable applicational properties can be prepared.

By contrast, the molecules of mesogenic compounds which have hitherto achieved technical importance in display technology and as temperature displays have an elongate form (cf. K. J. Toyne in Thermotropic Liquid Crystals, John Wiley & Sons, Ed., G. W. Gray, 1987, pp. 28ff); these form nematic, cholesteric and smectic phases. In addition, thermotropic liquid-crystalline phases are formed by diskoid molecules (cf. C. Destrade et al., Mol. Cryst. Liq. Cryst. Vol. 106, p.121 (1984)).

SUMMARY OF THE INVENTION

Surprisingly, it has now been found that, in particular, the tetrasubstituted methanes of the general formula $$C[Sp-A-(Z_1-A_1)_m-(Z_2-A_2)_n-R]_4, \quad (II)$$

in which —A—(Z$_1$—A$_1$)$_m$—(Z$_2$—A$_2$)$_n$— is M, Z$_1$ and Z$_2$ are each, independently of one another, —CH$_2$CH$_2$—, —COO—, —OOC—, —OCH$_2$—, CH$_2$O —, —C≡C—, —N=N— or a single bond;

A, A$_1$ and A$_2$ are each, independently of one another, a 1,4-phenylene radical which is unsubstituted or monosubstituted to tetrasubstituted by fluorine or chlorine and in which, in addition, one or two CH groups may be replaced by N, or are a 1,4-cyclohexylene radical which has, in particular, a trans-configuration and in which, in addition, one or two non-adjacent CH$_2$ groups may be replaced by —O—, or are a piperidine-1,4-diyl radical or a 1,4-bicyclo[2.2.2]octylene radical; and n and m are each, independently of one another, 0 or 1, with the proviso that m or n is 1 at least once in one of the four substituents of the methane, and Sp and R are as defined above, are distinguished by high transition temperatures from the liquid-crystalline state to the isotropic phase (clearing point). Consequently, they are highly suitable for use as chemically stable components in liquid-crystalline media which are themselves suitable, due to their favorable optical and dielectric anisotropies, for the production of electro-optical displays, especially as they are chemically and thermally stable.

DESCRIPTION OF THE INVENTION

As is known, such devices are based on the change in the preferential direction of the molecular alignment, which is determined by surface effects, by an electric field. The plane of vibration of polarized light can thereby be rotated or the absorption of dissolved dichroic dyes can be changed. In addition, liquid-crystalline media having advantageous optical properties can be prepared for the production of temperature displays, which are based on selective reflection of natural light (cf. H. Kelker et al., Chem. Ing. Tech., Vol.45, p.1005 (1973)). The novel compounds which contain optically active carbon atoms in one or more radicals R, Sp, Z$_1$ and Z$_2$ are suitable for this purpose.

Furthermore, optical storage elements which can be erased by means of the liquid-crystalline media according to the invention can be produced. The principle of such devices is described in D. Coates, Thermotropic Liquid Crystals, John Wiley & Sons, Ed. G. W. Gray, 1987, pp.99ff).

The compounds of the general formula II are furthermore distinguished by low volatility, which is connected to their comparatively high molecular weight. They can therefore also be used in nonlinear optical switching elements, in particular in Pockels cells and frequency doublers.

By means of a suitable choice of the substitution pattern of the compounds, high molecular second and third order hyperpolarizabilities can be obtained. In order to achieve second order macroscopic hyperpolarizability, it is known that a non-centrosymmetric arrangement of the molecules is necessary. The general correlations between molecular properties and applicational parameters are known (cf D. J. Williams et al., "Nonlinear Optical Properties of Organic Molecules and Crystals", Vol. 1, Academic Press, New York (1987), and G. G. Roberts, Adv. Phys., Vol.34, p.475 (1985)).

By means of the choice of the type of substituents, smectic and nematic media having favorable optical and dielectric properties or cholesteric media having suitable pitches of their helical structure can be obtained. In general, they are additionally distinguished by low vapor pressures due to their comparatively high molecular weight.

The compounds of the general formulae I and II are furthermore suitable as anisotropic matrices for spectroscopic studies.

The present invention thus furthermore relates to the use of the novel methane derivatives, in particular the compounds of the general formula II, as components of liquid-crystalline media, and to electro-optical display elements, temperature displays, optical memories and nonlinear optical switches containing such media.

The compounds of the general formulae I and II include methane derivatives containing four identical substituents —Sp—M—R or —[Sp—A—(Z₁—A₁)ₘ—(Z₂—A₂)ₙ—R] and those in which these substituents are different. Preference is given to methane derivatives which have three identical substituents (and one further different substituent). Particular preference is given to compounds which contain four identical substituents. The compounds of the formula II may contain from five to twelve cyclic structural elements.

The compounds containing identical methane substituents include compounds with two rings in each of the substituents, in accordance with the sub-formulae IIa and IIb:

$$C(Sp-A-A_1-R)_4 \tag{IIa}$$

$$C(Sp-A-Z_1-A_1-R)_4 \tag{IIb}$$

and with three rings in each of the substituents, in accordance with the sub-formulae:

$$C(Sp-A-A_1-A_2-R)_4 \tag{IIc}$$

$$C(Sp-A-Z_1-A_1-A_2-R)_4 \tag{IId}$$

$$C(Sp-A-Z_1-A_1-Z_2A_2-R)_4 \tag{IIe}$$

$$C(Sp-A-A_1-Z_2-A_2-R)_4 \tag{IIf}$$

Of these, those of the sub-formulae IIa, IIb and IIc are particularly preferred. The symbols R, A, A₁, A₂, Sp, Z₁, Z₂, m and n are as defined above. The cyclic structural elements A, A₁ and A₂ in the formula II are shown in simplified form below: PH is a 1,4-phenylene group, CY is a 1,4-cyclohexylene group and PY is a pyrimidine-2,5-diyl group, it also being possible for these structural elements to be substituted by fluorine or chlorine.

The compounds of the sub-formula IIa include the preferred sub-formulae IIaa to IIac $$C(Sp-PH-PH-R)_4 \tag{IIaa}$$

$$C(Sp-PH-CY-R)_4 \tag{IIab}$$

$$C(Sp-CY-CY-R)_4 \tag{IIac}$$

The compounds of the formula IIb include the preferred sub-formulae IIba and IIbb $$C(Sp-PH-CH_2-CH_2-CY-R)_4 \tag{IIba}$$

$$C(Sp-PH-COO-PH-R)_4 \tag{IIbb}$$

The compounds of the formula IIc include the preferred sub-formulae IIca to IIcc $$C(Sp-PH-PH-CY-R)_4 \tag{IIca}$$

$$C(Sp-PH-CY-CY-R)_4 \tag{IIcb}$$

$$C(Sp-PH-CY-CY-R)_4 \tag{IIcc}$$

Sp is preferably —CH₂O—, —CH₂OOC—, —CH₂O(CH₂)ᵣ—, —CH₂OOC(CH₂)ₛ—, where r and s are each 0 to 10, preferably 1 to 6, or is a single bond. Z₁ and Z₂ are each preferably a single bond or one of the radicals —CH₂CH₂—, —OOC— and —COO—.

In the above sub-formulae, R is preferably an alkyl, alkoxy or alkoxymethyl radical. If R is an alkyl radical, it may be straight-chain or branched. It is preferably unbranched and is methyl, ethyl, propyl, butyl, pentyl, hexyl or heptyl.

The 1,4-cyclohexylene groups of the formula II preferably have the trans-configuration.

The compounds of the formula II may contain one or more asymmetric carbon atoms. In this case, the formulae cover optically active enantiomers and enantiomer mixtures and racemates. Compounds of the formula II which contain groups R which are suitable for polymerization reactions are suitable for the preparation of liquid-crystalline polymers.

The novel compounds of the general formula II are prepared by processes which are known per se in general terms. These are indicated, for example, in the multivolume work Houben-Weyl, Methoden der organischen Chemie [Methods of Organic Chemistry], Georg Thieme Verlag, Stuttgart.

It is in many cases advantageous first to prepare precursors of the general formula III $$X-Sp-A-(Z_1-A_1)_m-(Z_2-A_2)_n-R \tag{III}$$

where X is a reactive group, and then to react these with a reactive tetrakis-substituted methane. If the methanes of the formula II according to the invention are to contain different substituents, the reactive groups of the methane are expediently converted one after the other with isolation of intermediates. If the reactive tetrakis-substituted methane employed is optically active, this method gives compounds of the formula II containing a chiral central atom. If a plurality of precursors of the formula III are reacted simultaneously, complex mixtures of compounds of the formula II, which may have applicational advantages due to their low melting points, are obtained.

Compounds of the formula II which contain the ester group —OOC— or —COO— can be prepared in a manner known in general terms by reacting alcohols with carboxylic acid halides or carboxylic anhydrides. The ether groups —CH₂O— or —OCH₂— are prepared by reacting alkyl halides or alkyl tosylates with metal alkoxides or metal phenoxides. In a special process, tetraethers of pentaerythritol can be prepared by phase-transfer catalysis from pentaerythritol and alkyl bromides by the method of Nouguier and Mchich (J.Org. Chem., Vol.50, p.3296 (1985)).

Direct linking of aryloxy radicals to the central carbon atom is expediently accomplished by reacting copper phenoxides with tetrachloromethane (Can. J.Chem., Vol.57, p.890 (1979)). Orthoesters of the type C(O—Z₀—A—Z₁—Z₂—A₂—R)₄ (Z₀=alkylene or a single bond) are prepared by transesterification by processes known in general terms.

Compounds of the formulae II and III can be prepared in a manner known per se, for example by reduction of precursors in the synthesis, —CO— being converted into —CH₂— or —HCOH— groups, —CH=

CH— into —CH$_2$CH$_2$—groups, —C≡C— into —CH$_2$CH$_2$—groups and aromatic rings into alicyclic or heteroalicyclic rings.

Thus, ketones and aldehydes can be converted into the corresponding hydrocarbons by the Wolff-Kishner method in alkaline solution using hydrazine hydrate. The reduction by means of gaseous hydrogen is carried out in the presence of a catalyst at temperatures between 0° and 200° C. and at pressures between about 1 and 200 bar in solvents such as ethanol, tetrahydrofuran or glacial acetic acid. Suitable catalysts are platinum and palladium or alternatively Raney nickel. The conversion of carbonyl compounds into alcohols is expediently carried out by reduction using complex hydrides, such as LiAlH$_4$ or NaBH$_4$.

Aromatic precursors of the compounds of the formulae II and III can be converted by electrophylic substitutions which are known in general terms. A preferred reaction is the Friedel-Crafts acylation. The aromatic compound here is converted into a ketone in dichloromethane by means of a complex formed from aluminum chloride and an acyl chloride.

Nitriles of the formulae II and III are prepared by dehydration of amides using POCl$_3$ or SOCl$_2$ in dimethylformamide or toluene. The amides —CONH$_2$ are prepared from carboxylic acid halides or esters by reaction with ammonia. Of the precursors, the carboxylic acids are preferably prepared by oxidation of aldehydes or ketones. A preferred method is the known haloform reaction, in which compounds containing the —COCH$_3$ group are introduced into a highly alkaline solution of an alkali metal hypobromite. After acidification, carboxylic acids which can generally be crystallized readily are obtained.

The liquid-crystalline media according to the invention contain at least one of the compounds of the formula I, in particular II. Preference is given to mixtures containing from 2 to 10 such compounds. The proportion of such mixtures made up by these compounds is between 1 and 100% by weight. Preference is given to a proportion of from 30 to 98% by weight. The compounds of the formula II may be enantiotropic or monotropic liquid-crystalline. In addition to compounds of the formulae I and II, media according to the invention may also contain known enantiotropic or monotropic liquid-crystalline compounds which, in pure form, form nematic, cholesteric, smectic, diskotic or phasmidic phases. They are preferably selected from the classes of the substituted phenylcyclohexanes, biphenyls, bicyclohexyls, phenylbicyclo[2.2.2]octanes, phenyl cyclohexylcarboxylates, phenyl benzoates, N-benzylidenanilines, azobenzenes, phenylpyridines, phenyl- or cyclohexylpyrimidines, tolans, bicyclohexylphenyls, cyclohexylbiphenyls and dicyclohexylbiphenyls. These mixture components may also be polymeric liquid-crystalline compounds.

In addition, the liquid-crystalline media according to the invention may contain further conventional additives, such as, for example, dichroic dyes for color displays, antioxidants and non-mesomorphic organic compounds in order to reduce the viscosity. In addition, optically active additives are suitable.

The liquid-crystalline media according to the invention are prepared in a manner known per se. The components are usually dissolved in one another, advantageously at elevated temperature.

The examples below illustrate the invention in greater detail without representing a limitation. In these examples, m.p.=melting point, c.p.=clearing point. Above and below, percentages are percent by weight; all temperatures are indicated in degrees celsius. "Conventional work-up" means that water is added, the mixture is extracted with methylene chloride, the phases are separated, the organic phase is dried and evaporated, and the product is purified by crystallization and/or chromatography.

EXAMPLES 1 to 7

1.) 19.0 g of anhydrous aluminum chloride are covered with 75 ml of dichloromethane with exclusion of moisture. 6.5 g of succinic anhydride are added in portions with stirring and with ice cooling. A solution of 20 g of the known compound 4-trans-(4-pentylcyclohexyl)biphenyl in 50 ml of dichloromethane is added dropwise, during which the temperature of the reaction mixture must not exceed 10°. Conventional work-up (recrystallization from glacial acetic acid) gives 19.5 g of 4-oxo-4-[4'-trans-(4-pentylcyclohexyl)biphenyl-4-yl]butyric acid, m.p 215°, c.p. >320°.

16.0 g of this acid are dissolved in a mixture of 250 ml of tetrahydrofuran and 50 ml of ethanol. The hydrogenation is carried out at atmospheric pressure and room temperature after addition of 0.8 g of palladium catalyst (5% of Pd on activated charcoal). The take-up of hydrogen is complete after 20 hours. The catalyst is filtered off, the solvent is removed by distillation, and the residue is recrystallized from glacial acetic acid. Yield: 9.3 g of 4-[4'-trans-(4-pentylcyclohexyl)biphenyl-4-yl]butyric acid, m.p 197°, c.p. 210°.

0.3 g of pentaerythritol is introduced into a melt of 4.0 g of the biphenylylbutyric acid at 210°. The mixture is stirred vigorously at this temperature for 4 hours. The cooled melt is dissolved in dichloromethane and purified by column chromatography (silica gel/dichloromethane). The residue obtained from the main fraction after removal of the solvent by distillation is recrystallized from 2-butanone. Yield: 1.5 g of tetrakis[4-(4'-trans-(4-pentylcyclohexyl)biphenyl-4-yl)butyryloxymethyl]-methane, m.p 226°, c.p. 283°.

The following are prepared in the same way, starting from the corresponding carboxylic acids and with the amounts matched to the molar ratios in Example 1:

2.) Tetrakis[4-trans-(4-pentylcyclohexyl)benzoyloxymethyl]methane, m.p. 99°.

3.) Tetrakis[4'-propylbiphenyl-4-yl-acetyloxymethyl]-methane, m.p. 168 °, c.p. 130°.

4.) Tetrakis [4- (4'-pentyl-biphenyl-4-yl)butyryloxymethyl]methane, m.p 143°, c.p. 120°.

5.) Tetrakis[4'pentyl-trans,trans-bicyclohexyl-4-yl-carbonyloxymethyl]methane, m.p. 135°.

6.) Tetrakis[5- (4'-cyano-biphenyl-4-yl)valeryloxymethyl]methane.

7.) The following is prepared starting from phenyltris[hydroxymethyl]methane and 4-[4'-trans-(4-pentylcyclohexyl)biphenyl-4-yl]butyric acid: phenyltris[4-(4'-trans-(4-pentylcyclohexyl)biphenyl-4-yl)butyryloxymethyl]methane.

EXAMPLES 8 and 9

8.) 5.0 g of the known compound 4-(5-heptyl-2-pyrimidyl)phenol are dissolved in 70 ml of dimethyl sulfoxide together with 1.35 g of pentaerythrityl tetrabromide. 15 g of finely powdered potassium carbonate are added, and the mixture is stirred at 80° C. for 16 h. Conventional work-up gives 2.1 g of tetrakis[4-(5-heptyl-2-pyrimidyl)phenyloxymethyl]methane, m.p. 179°.

9.) In the same way, starting from pentaerythrity tetrabromide and 4-(4-decyloxybenzoyloxy)phenol, tetrakis [4-(4-decyloxybenzoyloxy)phenyloxymethyl]methane is prepared.

EXAMPLE 10 (use example)

A liquid-crystalline medium comprising 20.0% of tetrakis[4-(4'-pentylbiphenyl-4-yl)butyryloxymethyl]methane 27.5% of tetrakis[4'-propylbiphenyl-4-yl-acetoxymethyl]methane 49.0% of 4'-trans-(4-pentylcyclohexyl)biphenyl-4-yl-carbonitrile 3.5% of 4,4'-bis[trans-4-propylcyclohexyl]-2-fluorobiphenyl has a smectic A to nematic transition at 143° C. and a nematic to liquid transition at 151°. The smectic phase is supercoolable to room temperature. Due to its positive dielectric anisotropy, it is advantageously suitable for use in an erasable optical memory element. On cooling a thin layer of the medium from the nematic to the smectic phase in a sufficiently strong electric field, the layer remains transparent. On cooling without an electric field, the layer is highly light-scattering.

I claim:

1. A methane derivative of the general formula

 (I)

in which the radicals —Sp—M—R' can be identical or different and where

Sp is, in each case independently of the other cases, is an alkylene or alkenylene radical having up to 12 carbon atoms which is unsubstituted or monosubstituted by halogen, —CN or —CF$_3$ and in which, in addition, one or two non-adjacent CH$_2$ groups can be replaced by —O—, —CO—, —COO—, —OOC—, —CONH— or —OCOO—, or is a single bond;

M is a mesogenic group of the general formula —A—(Z$_1$—A$_1$)$_m$—(Z$_2$—A$_2$)$_n$— in which Z$_1$ and Z$_2$ are each, independently of one another, —CH$_2$CH$_2$—, —COO—, —OOC—, —OCH$_2$—, CH$_2$O—, —C≡C—, —N=N— or a single bond;

A, A$_1$ and A$_2$ are each, independently of one another, a 1,4- phenylene radical which is unsubstituted or monosubstituted to tetrasubstituted by fluorine or chlorine and in which, in addition, one or two CH groups can be replaced by N, or are a 1,4-cyclohexylene radical which has, in particular, a trans-configuration and in which, in addition, one or two non-adjacent CH$_2$ groups can be replaced by —O—, or are a piperidine-1,4-diyl radical or a 1,4-bicyclo[2.2.2]octylene radical; and n and m are each, independently of one another, 0 or 1, with the proviso that m or n is 1 at least once in one of the four substituents of the methane; and R is hydrogen, halogen, —CN, —CF$_3$, —OCF$_3$, —NO$_2$, —N(CH$_3$)$_2$, a straight-chain or branched alkyl or alkenyl radical having up to 12 carbon atoms which is unsubstituted or monosubstituted or polysubstituted by —CN, —NH$_2$, —CF$_3$ or haloogen and in which one or more non-adjacent CH$_2$ groups can be replaced by the radicals —O—, —CO—, —COO—, —OOC— or —OCOO—.

2. A methane derivative as claimed in claim 1, wherein Sp is a radical of the formula —CH$_2$COO(CH$_2$)$_r$— or —CH$_2$O(CH$_2$)$_s$, where r and s can be the numbers 0 to 10.

3. A methane derivative as claimed in claim 1, wherein A, A$_1$ and/or A$_2$ are a 1,4-phenylene radical, a 1,4-cyclohexylene radical or a pyrimidine-2,5-diyl radical.

4. A methane derivative as claimed in claim 1, wherein Z$_1$ and Z$_2$ are each a single bond or one of the radicals —CH$_2$CH$_2$—, —COO— and —CH$_2$O—.

5. A methane derivative as claimed in claim 1, wherein R is an alkyl group having 1 to 12 carbon atoms, —CN or —F.

6. A methane derivative as claimed in claim 1, wherein three substituents —[Sp—A—(Z$_1$—A$_1$)$_m$—(Z$_2$—A$_2$)$_n$—R]— are identical.

7. A methane derivative as claimed in claim 1, wherein all four substituents —[Sp—A—(Z$_1$—A$_1$)$_m$—(A$_2$—A$_2$)$_n$—R]— are identical.

8. A methane derivative as claimed in claim 7, wherein Z$_1$ is a single bond, m=1 and N=zero.

9. A methane derivative as claimed in claim 7, wherein m=1 and n=zero.

10. A methane derivative as claimed in claim 7, wherein m and n=1, and Z$_1$ and Z$_2$ are single bonds.

11. A methane derivative as claimed in claim 7, wherein Sp is a single bond or one of the radicals —CH$_2$O, CH$_2$OOC—, —CH$_2$O(CH$_2$)$_r$— or —CH$_2$OOC(CH$_2$)$_s$, where r and s can be the numbers 0 to 10.

12. A methane derivative as claimed in claim 7, wherein R is a straight chain or branched, alkyl radical, an alkoxy radical or an alkoxy methyl radical.

13. A methane derivative as claimed in claim 12, wherein R is a straight chain alkyl radical having 1 to 7 carbon atoms.

14. A liquid-crystalline medium containing the compound of claim 1.

15. An electro-optical display element containing the liquid crystalline medium of claim 14.

16. A temperature display device based on selective light reflection containing the liquid crystalline medium of claim 14.

17. An optical memory element containing the liquid crystalline medium of claim 14.

18. A non-linear optical switching element containing the liquid crystalline medium of claim 14.

* * * * *